United States Patent [19]
Glazer

[11] Patent Number: 5,962,426
[45] Date of Patent: Oct. 5, 1999

[54] TRIPLE-HELIX FORMING OLIGONUCLEOTIDES FOR TARGETED MUTAGENESIS

[75] Inventor: Peter M. Glazer, Guilford, Conn.

[73] Assignee: Yale University, New Haven, Conn.

[21] Appl. No.: 08/476,712

[22] Filed: Jun. 7, 1995

Related U.S. Application Data

[63] Continuation-in-part of application No. 08/083,088, Jun. 25, 1993.
[51] Int. Cl.[6] .................... A16K 48/00; C07H 21/04; C12Q 1/68
[52] U.S. Cl. .................... 514/44; 536/23.1; 536/24.3; 536/25.3; 536/24.5; 435/6
[58] Field of Search ............................ 514/44; 536/23.1, 536/24.3, 25.3, 245; 435/6; 935/6, 10, 33, 36

[56] References Cited

U.S. PATENT DOCUMENTS 5,176,996  1/1993  Hogan ........................................ 435/6

FOREIGN PATENT DOCUMENTS

| AO 266 0990 | 5/1988 | European Pat. Off. . |
| AO 375 408 | 6/1990 | European Pat. Off. . |
| WO 95/013650 | 1/1995 | WIPO . |

OTHER PUBLICATIONS

Wang et al, Molecular and Cellular Biology (Mar., 1995) 15 : 1759–1768.
Rooney et al, Proceedings National Academy of Sciences USA (Mar. 1995) 92: 2141–2144.
Beal and Dervan, "The Influence Of Single Base Triplet Changes On The Stability Of Pur–Pur–Pyr Triple Helix Determined By Affinity Cleaving", Nuc. Acids Res., 11:2773 (1992).
Beal and Dervan, "Second Structural Motif For Recognition Of DNA by Oligonucleotide–Directed Triple–Helix Formation," Science, 251:1360–1363 (1991).
Blume et al., "Triple Helix Formation by Purine–Rich Oligonucleotides Targeted To The Human Dihydrofolate Reductase Promoter", Nucleic Acids Res., 20:1777 (1992).
Cooney et al., "Site–Specific Oligonucleotide Binding Represses Transcription Of The Human c–mvc Gene In Vitro", Science, 241:456 (1988).
Durland et al., "Binding Of Triple Helix Forming Oligonucleotides to Sites In Gene Promoters", Biochemistry, 30:9246 (1991).
Duval–Valentin et al., "Specific Inhibition Of Transcription By Triple Helix–Forming Oligonucleotides", Proc. Natl. Acad. Sci. USA, 89:504 (1992).
Francois et al., "Sequence–Specific Recognition And Cleavage Of Duplex DNA via Triple–Helix Formation By Oligonucletides Covalently Linked To A Phenanthroline–Copper Chelate", Proc. Natl. Acad. Sci. USA, 86:9702 (1989).
Gasparro, Francis P., et al., "Site–specific targeting of psoralen photoadducts with a triple helix–forming oligonucleotide: characterization of psoralen monoadduct and crosslink formation," Nucleic Acids Res. 22:2845–2852(1994).

(List continued on next page.)

*Primary Examiner*—Carla J. Myers
*Attorney, Agent, or Firm*—Arnall Golden & Gregory, LLP

[57] ABSTRACT

A high affinity, triplex-forming oligonucleotide and methods for use thereof wherein an oligonucleotide is used to form a triple-stranded nucleic acid molecule with a specific DNA segment of a target DNA molecule. Upon formation of the triplex, the binding of the oligonucleotide stimulates mutagenesis within or adjacent to the target sequence using cellular DNA synthesis or repair mechanisms. The mutation activates, inactivates or alters the activity and function of the target molecule.

11 Claims, 2 Drawing Sheets

OTHER PUBLICATIONS

Giovannangeli, Carine, et al., "Oligodeoxynucleotide–directed photo–induced cross–linking of HIV proviral DNA via triple–helix formation," *Nucleic Acids Res.* 20:4275–4281(1992).

Grigoriev, Mikhail, et al., "Inhibition of gene expression by triple helix–directed DNA cross–linking at specific sites," *Proc. Natl. Acad. Sci.* 90:3501–3505(1993).

Glazer et al., "Detection And Analysis Of UV–Induced Mutations In Mammalian Cell DNA Using A Phage Suttle Vector", *Proc. Natl. Acad. Sci. USA,* 83:1041–1044 (1986).

Grigoriev et al., "A Triple Helix–Forming Oligonucleotide–Intercalator Conjugate Acts As A Transcriptional Repressor via Inhibition Of NF B Binding To Interleukin–2 Receptor a–Regulatory Sequence", *J. of Biological Chem.,* 267:3389 (1992).

Havre, Pamela A., et al., "Targeted mutagenesis of DNA using triple helix–forming oligonucleotides linked to psoralen," *Proc. Natl. Acad. Sci.* 90:7879–7883(1993).

Ito et al., "Sequence–Specific DNA Purification By Triplex Affinity Capture", *Proc. Natl. Acad. Sci. USA,* 89:495 (1992).

Lin et al., "Use Of EDTA Derivatization To Characterize Interactions Between Oligodeoxyribonucleoside Methylphosphonated And Nucleic Acids", *Biochemistry,* 28:1054 (1989).

Maher et al., "Inhibition Of DNA Binding Proteins By Oligonucleotide–Directed Triple Helix Formation", *Science,* 245:725 (1989).

Maher et al., "Analysis Of Promoter–Specific Repression By Triple Helical DNA Complexes In A Eukaryotic Cell–Free Transcription System", *Biochemistry,* 31:70 (1992).

Mergny et al., "Sequence Specificity In Triple–Helix Formation: Experimental And Theoretical Studies Of The Effect Of Mismatches On Triplex Stability", *Biochemistry,* 30:9791 (1991).

Mirabelli, C. K., et al., In Vitro and In Vivo Pharmacologic Activities of Antisense Oligonucleotides, *Anti–Cancer Drug Design* 6:647–661 (Dec., 1991).

Moser and Dervan, "Sequence–Specific Cleavage Of Double Helical DNA By Triple Helix Formation", *Science,* 238:645 (1987)Orson et al., "Oligonucleotide Inhibition Of IL2Ra mRNA Transcription By Promoter Region Collinear Triplexed Formation In Lymphocytes", *Nucleic Acids Res.,* 19:3435 (1991).

Pei et al., "Site–Specific Cleavage Of Duplex DNA By A Semisynthetic Nuclease via Triple–Helix Formation", *Proc. Natl. Acad. Sci. USA,* 87:9858 (1990).

Perrouault et al., "Sequence–Specific Artificial Photo–Induced Endonuclease Based On Triple Helix–Forming Oligonucleotides", *Nature,* 344:358 (1990).

Postal et al., "Evidence That A Triple–Forming Oligodeoxyribonucleotide Binds To The c–myc Promoter In HeLA Cells, Thereby Reducing cmyc mRNA Levels", *Proc. Natl. Acad. Sci. USA,* 88:8227(1991).

Posvic and Dervan, "Sequence–Specific Alkylation Of Double Helical DNA By Oligonucleotide–Directed Triple–Helix Formation", *J. Am. Chem Soc.,* 112:9428 (1992).

Praseuth et al., "Sequence–Specific Binding And Photo-crosslinking Of a and β Oligodeoxyribonucleotide To The Major Groove Of DNA via Triple–Helix Formation", *Proc. Natl. Acad. Sci. USA,* 85:1349 (1988).

Strobel et al., "Site–Specific Cleavage Of Human Chromosome Mediated By Triple–Helix Formation", *Science,* 254:1639 (1991).

Takasugi et al., "Sequence–Specific Photo–Induced Cross–Linking Of The Two Strands Of Double–Helical DNA By A Psoralen Covalently Linked To A Triple Helix–Forming Oligonucleotide", *Proc. Natl. Acad. Sci. USA,* 88:5602–5606 (1991).

Uhlmann, E., et al., "Antisense Oligonucleotides: A New Therapeutic Principle," *Chemical Reviews,* 90(4):544–584 (Jun., 1990).

Wood, et al., "The Effect Of Volume And Temperature On The Energy And Entropy Of Pure Liquids", *J. Am. Chem. Soc.,* 79–2023 (1957).

Young et al., "Triple Helix Formation Inhibits Transcription Elongation in vitro", *Proc. Natl. Acad. Sci. USA,* 88:10023 (1991).

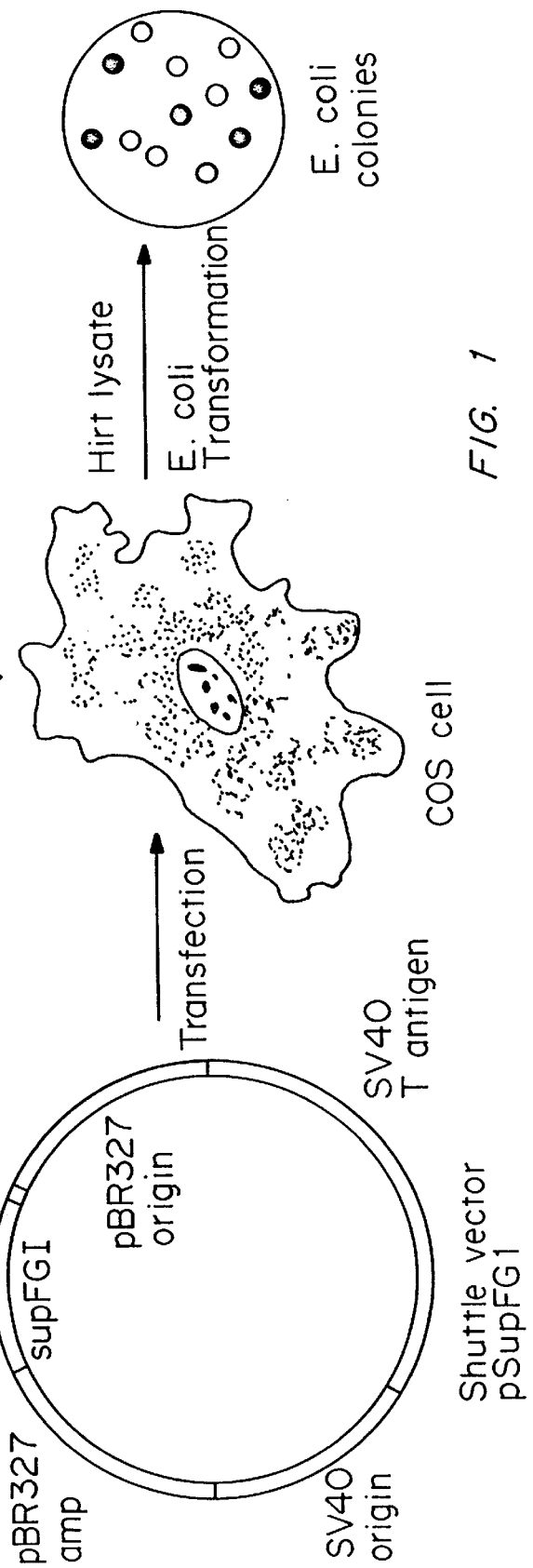

Multiple point mutations

```
                                                                    225 C->G
                                                                    199 C->T
                                                                    215 G->A

A                A
                                    A                A
                                    G

I       IA                 C    A
                G       A                  C    A A
                T       T         T        GA

3'                                                                                                                  5'
CTTAAGCTCTCGGGACGAGCTCGACACCACCCCAAGGGCTCGCCGGTTTCCCTCGTCTGAGATTTAGAC GGCAGTAGCTGAAGCTTCCAAGCTTAGGAAGGGGGGGTGGGGTGGGGGAGGGGGAG
          80         90         100        110        120        130        140        150        160        170        180
GAATTCGAGAGCCCTGCTCGAGCTGTGGGTTCCCGAGCGGCCAAAGGGAGCAGACTCTAAATCTGCCGTCATGACTTCGAAGGTTCGAATCCTTCCCCCCCCCCACCACCCCCTCCCCCTC
5' pre-tRNA (58-98)       Suppressor tRNA (99-183)                                              Triplex binding site (Seq. ID No. 6)
```

Single point mutations

Deletions

TRIPLE-HELIX FORMING OLIGONUCLEOTIDES FOR TARGETED MUTAGENESIS

This application is a continuation-in-part of U.S. Ser. No. 08/083,088, filed Jun. 25, 1993.

The United States Government has certain rights in this invention by virtue of National Institutes of Health grant No. ES05775 to Peter M. Glazer.

BACKGROUND OF THE INVENTION

This relates to the fields of genetics, and more particularly relates to site-directed mutagenesis of a gene of interest.

Triple-stranded DNA

Since the initial observation of triple-stranded DNA many years ago by Felsenfeld et al., *J. Am. Chem. Soc.* 79:2023 (1957), oligonucleotide-directed triple helix formation has emerged as a valuable tool in molecular biology. Current knowledge suggests that oligonucleotides can bind as third strands of DNA in a sequence specific manner in the major groove in polypurine/polypyrimidine stretches in duplex DNA. In one motif, a polypyrimidine oligonucleotide binds in a direction parallel to the purine strand in the duplex, as described by Moser and Dervan, *Science* 238:645 (1987), Praseuth et al., *Proc. Natl. Acad. Sci. USA* 85:1349 (1988), and Mergny et al., *Biochemistry* 30:9791 (1991). In the alternate purine motif, a polypurine strand binds antiparallel to the purine strand, as described by Beal and Dervan, *Science* 251:1360 (1991). The specificity of triplex formation arises from base triplets (AAT and GGC in the purine motif) formed by hydrogen bonding; mismatches destabilize the triple helix, as described by Mergny et al., *Biochemistry* 30:9791 (1991) and Beal and Dervan, *Nuc. Acids Res.* 11:2773 (1992).

Triplex forming oligonucleotides have been found useful for several molecular biology techniques. For example, triplex forming oligonucleotides designed to bind to sites in gene promoters have been used to block DNA binding proteins and to block transcription both in vitro and in vivo. (Maher et al., *Science* 245:725 (1989), Orson et al., *Nucleic Acids Res.* 19:3435 (1991), Postal et al., *Proc. Natl. Acad. Sci. USA* 88:8227 (1991), Cooney et al., *Science* 241:456 (1988), Young et al., *Proc. Natl. Acad. Sci. USA* 88:10023 (1991), Maher et al., *Biochemistry* 31:70 (1992), Duval-Valentin et al., *Proc. Natl. Acad. Sci. USA* 89:504 (1992), Blume et al., *Nucleic Acids Res.* 20:1777 (1992), Durland et al., *Biochemistry* 30:9246 (1991), Grigoriev et al., *J. of Biological Chem.* 267:3389 (1992), and Takasugi et al., *Proc. Natl. Acad. Sci. USA* 88:5602 (1991)). Site specific cleavage of DNA has been achieved by using triplex forming oligonucleotides linked to reactive moieties such as EDTA-Fe(II) or by using triplex forming oligonucleotides in conjunction with DNA modifying enzymes (Perrouault et al., *Nature* 344:358 (1990), Francois et al., *Proc. Natl. Acad. Sci. USA* 86:9702 (1989), Lin et al., *Biochemistry* 28:1054 (1989), Pei et al., *Proc. Natl. Acad. Sci. USA* 87:9858 (1990), Strobel et al., *Science* 254:1639 (1991), and Posvic and Dervan, *J. Am. Chem Soc.* 112:9428 (1992)). Sequence specific DNA purification using triplex affinity capture has also been demonstrated. (Ito et al., *Proc. Natl. Acad. Sci. USA* 89:495 (1992)). Triplex forming oligonucleotides linked to intercalating agents such as acridine, or to crosslinking agents, such as p-azidophenacyl and psoralen, have been utilized, but only to enhance the stability of triplex binding. (Praseuth et al., *Proc. Natl. Acad. Sci. USA* 85:1349 (1988), Grigoriev et al., *J. of. Biological Chem.* 267:3389 (1992), Takasugi et al., *Proc. Natl. Acad. Sci. USA* 88:5602 (1991).

Gene Therapy

Gene therapy can be defined by the methods used to introduce hetergous DNA into a host cell or by the methods used to alter the expression of endogenous genes within a cell. As such, gene therapy methods can be used to alter the phenotype and/or genotype of a cell.

Methods which alter the genotype of a cell typically rely on the introduction into the cell of an entire replacement copy of a defective gene, a heterologous gene, or a small nucleic acid molecule such as an oligonucleotide, to treat human, animal and plant genetic disorders. The introduced gene or nucleic acid molecule, via genetic recombination, replaces the endogenous gene. This approach requires complex delivery systems to introduce the replacement gene into the cell, such as genetically engineered viruses, or viral vectors.

Alternatively, gene therapy methods can be used to alter the expression of an endogenous gene. One example of this type of method is the field of antisense therapy. In antisense therapy, a nucleic acid molecule is introduced into a cell, the nucleic acid molecule being of a specific nucleic acid sequence so as to hybridize or bind to the mRNA encoding a specific protein. The binding of the antisense molecule to an mRNA species decreases the efficiency and rate of translation of the mRNA.

Gene therapy is being used on an experimental basis to treat well known genetic disorders of humans such as retinoblastoma, cystic fibrosis, and sickle cell anemia. However, in vivo efficiency is low due to the limited number of recombination events actually resulting in replacement of the defective gene.

A method for targeted mutagenesis of a target DNA molecule would be useful as another means of gene therapy which can be carried out in vivo. Such a method would also be a useful research tool for genetic engineering or for studying genetic mechanisms such as DNA repair.

Therefore, it is an object of the present invention to provide a method for in vivo and in vitro targeted mutagenesis of a target DNA molecule.

It is a further object of the present invention to provide a method for mutagenesis of a target DNA molecule that is highly specific and efficient.

It is a further object of the present invention to provide a method for treating genetic disorders by gene therapy without the need for a viral vector.

It is a further object of the present invention to provide a method for treating cancer.

It is a further object of the present invention to provide oligonucleotides for use in therapy and research.

SUMMARY OF THE INVENTION

High affinity, triplex-forming oligonucleotides and methods for use thereof are described herein. A high affinity oligonucleotide ($K_d \leq 2 \times 10^{-8}$) which forms a triple strand with a specific DNA segment of a target gene DNA is generated. The oligonucleotide binds/hybridizes to a target sequence within a target gene or target region of a chromosome, forming a triplex region. The binding of the oligonucleotide to the target region stimulates mutations within or adjacent to the target region using cellular DNA synthesis, recombination, and repair mechanisms. The mutation generated activates, inactivates, or alters the activity and function of the target gene.

If the target gene contains a mutation that is the cause of a genetic disorder, then the oligonucleotide is useful for mutagenic repair that restores the DNA sequence of the target gene to normal. If the target gene is a viral gene needed for viral survival or reproduction or an oncogene causing unregulated proliferation, such as in a cancer cell, then the mutagenic oligonucleotide is useful for causing a mutation that inactivates the gene to incapacitate or prevent reproduction of the virus or to terminate or reduce the uncontrolled proliferation of the cancer cell. The mutagenic oligonucleotide is also a useful anti-cancer agent for activating a repressor gene that has lost its ability to repress proliferation.

The triplex-forming oligonucleotide is also particularly useful as a molecular biology research tool to cause targeted mutagenesis. Targeted mutagenesis is useful for targeting a normal gene and for the study of mechanisms such as DNA repair. Targeted mutagenesis of a specific gene in an animal oocyte, such as a mouse oocyte, provides a useful and powerful tool for genetic engineering for research and therapy and for generation of new strains of "transmutated" animals and plants for research and agriculture.

BRIEF DESCRIPTION OF THE DRAWINGS

FIG. 1. Shuttle vector protocol to detect intracellular triple-helix-induced mutagenesis (Seq ID Nos. 1–5).

FIG. 2. Sequences of supFG1 mutations induced by triple helix formation in COS cells. (Seq. ID No. 6)

DETAILED DESCRIPTION OF THE INVENTION

High affinity, triplex-forming oligonucleotides and methods of use in gene therapy, anti-viral therapeutics, scientific research, and genetic engineering of cells, animals and plants are provided. The oligonucleotides herein described bind with specificity to a chosen site in a target DNA molecule, forming a triplex region. The, triplex acts to stimulate mutagenesis within or adjacent to the target region.

The mutation activates, inactivates or alters the activity and function of a gene containing the target site.

The triplex-forming oligonucleotides herein described can further be used to stimulate homologous recombination of a separate heterologous DNA fragment into the target region. The oligonucleotide activates cellular DNA synthesis, recombination, and repair mechanisms through triple helix formation. The activated cellular mechanisms can be directed to recombine a second heterologous DNA fragment into the target region.

Oligonucleotides

The oligonucleotides herein described are synthetic or isolated nucleic acid molecules which selectively bind to or hybridize with a predetermined region of a double-stranded DNA molecule so as to form a triple-stranded structure. The predetermined region is referred to herein as the target sequence or target region.

Preferably, the target region of the double-stranded molecule contains or is adjacent to a defective or essential portion of a target gene, such as the site of a mutation causing a genetic defect, a site causing oncogene activation, or a site causing the inhibition or inactivation of an oncogene suppressor. Most preferably, the gene is a human gene.

Preferably, the oligonucleotide is a single-stranded nucleic acid molecule between 7 and 40 nucleotides in length, most preferably 10 to 20 nucleotides in length for in vitro mutagenesis and 20 to 30 nucleotides in length for in vivo mutagenesis. The base composition is preferably homopurine or homopyrimidine. Alternatively, the base composition is polypurine or polypyrimidine. However, other compositions are also useful.

The oligonucleotides herein described are preferably generated using known DNA synthesis procedures. In the Example that follows, the oligonucleotides were obtained from a commercial supplier.

The nucleotide sequence of the oligonucleotides herein described is selected based on the sequence of the target sequence, the physical constraints imposed by the need to achieve binding of the oligonucleotide within the major groove of the target region, and the need to have a low dissociation constant ($K_d$) for the oligonucleotide/target sequence. The oligonucleotides will have a base composition which is conducive to triple-helix formation and will be generated based on one of the known structural motifs for third strand binding. In the motif used in the Example which follows (the anti-parallel purine motif), a G is used when there is a GC pair and an A is used when there is a AT pair in the target sequence. When there is an inversion, a CG or TA pair, another residue is used, for example, a T is used for a TA pair. A review of base compositions for third strand binding oligonucleotides is provided in U.S. Pat. No. 5,422,251.

Preferably, the oligonucleotide binds/hybridize to the target nucleic acid molecule under conditions of high stringency and specificity. Most preferably, the oligonucleotides bind in a sequence-specific manner within the major groove of duplex DNA. Reaction conditions for in vitro triple helix formation of an oligonucleotide probe or primer to a nucleic acid sequence vary from oligonucleotide to oligonucleotide, depending on factors such as oligonucleotide length, the number of G:C and A:T base pairs, and the composition of the buffer utilized in the hybridization reaction. An oligonucleotide substantially complementary, based on the third strand binding code, to the target region of the double-stranded nucleic acid molecule is preferred.

As used herein, an oligonucleotide is said to be substantially complementary to a target region when the oligonucleotide has a base composition which allows for the formation of a triple-helix with the target region. As such, an oligonucleotide is substantially complementary to a target region even when there are non-complementary bases present in the oligonucleotide. As stated above, there are a variety of structural motifs available which can be used to determine the nucleotide sequence of a substantially complementary oligonucleotide.

The preferred conditions under which a triple-stranded structure will form are standard assay conditions for in vitro mutagenesis and physiological conditions for in vivo mutagenesis. (See for example, Moser and Dervan, *Science* 238:645 (1987); Praseuth et al., *Proc. Natl. Acad. Sci. USA* 85:1349 (1988); Mergny et al., *Biochemistry* 30:9791 (1991); Beal and Dervan, *Science* 251:1360 (1991); Mergny et al., *Biochemistry* 30:9791 (1991) and Beal and Dervan, *Nuc. Acids Res.* 11:2773 (1992), which are incorporated by reference herein.)

A useful measure of triple helix formation is the equilibrium dissociation constant, $K_d$, of the triplex, which can be estimated as the concentration of oligonucleotide at which triplex formation is half-maximal. Preferably, the oligonucleotide has a binding affinity for the target sequence in the range of physiologic interactions. The preferred oligonucleotide has a $K_d$ less than or equal to approximately $10^{-7}$ M. Most preferably, the $K_d$ is less than or equal to $2 \times 10^{-8}$ M in order to achieve significant intracellular interactions.

A variety of methods are available to determine the $K_d$ of an oligonucleotide/target pair. In the Example which follows, the $K_d$ was estimated using a gel mobility shift assay (R. H. Durland et al., *Biochemistry* 30, 9246 (1991)). In this method, two complementary 57-mers containing the sequence corresponding to bp 157 to 213 of supFG1 were annealed to make a duplex target. The purine-rich oligonucleotide was end-labeled with $\alpha$-$[P^{32}]$-ATP and T4 polynucleotide kinase, mixed with the unlabeled complementary pyrimidine-rich 57-mer at a 1:1 ratio in Tris-EDTA buffer (TE buffer, 10 mM Tris (pH 7.4), 1 mM EDTA), incubated at 65° C. for 15 minutes and cooled to room temperature. A fixed concentration of duplex DNA ($5 \times 10^{-9}$ M) was incubated with increasing concentrations of oligonucleotides in 10 $\mu$l of 10 mM Tris (pH 7.4), 1 mM spermidine, and 20 mM $MgCl_2$ at 37° C. for 2 hours. The samples were analyzed by electrophoresis in an 8% polyacrylamide gel containing 89 mM Tris HCl, 89 mM boric acid, and 20 mM $MgCl_2$ at 5 V/cm for 15 hours, followed by autoradiography. A Phosphor-Imager (Molecular Dynamics, Sunnyvale, Calif.) was used for quantitation. The oligonucleotide concentration at which the triplex formation was half-maximal was taken as the equilibrium dissociation constant (Kd). A fixed concentration of the $P^{32}$-labeled 57 bp duplex ($5 \times 10^{-9}$ M) was incubated with increasing concentrations of each oligonucleotide as indicated, for 2 hours at 37° C. The samples were analyzed by electrophoresis in an 8% polyacrylamide gel in a buffer containing 20 mM $MgCl_2$ to maintain triplex stability, followed by autoradiography.

As described in the Examples, the triplex-forming oligonucleotides herein described can have a ribose/phosphodiester backbone, or can have a different sugar/bond than that found in DNA. For example, the oligonucleotide can contain a phosphorothioate internucleoside linkage. Such an oligonucleotide has been shown to be more stable in vivo.

The oligonucleotide can further be end capped to prevent degradation using a 3' propylamine group. Procedures for 3' or 5' capping oligonucleotides are well known in the art.

Method of Administration

Preferably, the oligonucleotides are dissolved in a physiologically-acceptable carrier, such as an aqueous solution or are incorporated within liposomes, and the carrier or liposomes are injected into the organism undergoing genetic manipulation, such as an animal requiring gene therapy or anti-viral therapeutics. The preferred route of injection in mammals is intravenous. It will be understood by those skilled in the art that oligonucleotides are taken up by cells and tissues in animals such as mice without special delivery methods, vehicles or solutions.

For in vitro research studies, a solution containing the oligonucleotides is added directly to a solution containing the DNA molecules of interest in accordance with methods well known to those skilled in the art and described in more detail in the examples below. In vivo research studies are conducted by transfecting cells with plasmid DNA and incubating the oligonucleotide in a solution such as growth media with the transfected cells for a sufficient amount of time for entry of the oligonucleotide into the cells for triplex formation. The transfected cells may be in suspension or in a monolayer attached to a solid phase, or may be cells within a tissue wherein the oligonucleotide is in the extracellular fluid.

For in vitro research studies, a solution containing the oligonucleotides is added directly to a solution containing the DNA molecules of interest in accordance with methods well known to those skilled in the art and described in more detail in the examples below.

As described above, the oligonucleotide can be made in a fashion so as to increase the stability of the oligomer under physiological conditions. Methods such as end capping and changing the sugar/linkage backbone of the oligonucleotide can be applied to the oligomers herein described to increase the serum half life of the oligonucleotide.

Methods of Use

If the target gene contains a mutation that is the cause of a genetic disorder, then the oligonucleotide is useful for mutagenic repair that may restore the DNA sequence of the target gene to normal. If the target gene is an oncogene causing unregulated proliferation, such as in a cancer cell, then the oligonucleotide is useful for causing a mutation that inactivates the gene and terminates or reduces the uncontrolled proliferation of the cell. The oligonucleotide is also a useful anti-cancer agent for activating a repressor gene that has lost its ability to repress proliferation. Furthermore, the oligonucleotide is useful as an antiviral agent when the oligonucleotide is specific for a portion of a viral genome necessary for proper proliferation or function of the virus.

The oligonucleotides herein described can be used alone or in combination with other mutagenic agents. As used herein, two agents are said to be used in combination when the two agents are co-administered, or when the two agents are administered in a fashion so that both agents are present within the cell or serum simultaneously. A preferred agent for co-administration is psoralen-linked oligonucleotides as described in PCT/US94/07234 by Yale University.

The oligonucleotides herein described can further be used to stimulate homologous recombination of a exogenously supplied, DNA fragment, into a target region. Specifically, by activating cellular mechanisms involved in DNA synthesis, repair and recombination, the oligonucleotides herein described can be used to increase the efficiency of targeted recombination.

In targeted recombination, a triplex forming oligonucleotide is administered to a cell in combination with a separate DNA fragment which minimally contains a sequence complementary to the target region or a region adjacent to the target region, referred to herein as the recombination fragment. The recombination fragment can further contain nucleic acid sequences which are to be inserted within the target region. The co-administration of a triplex forming oligonucleotide with the recombination fragment increases the frequency of insertion of the recombination fragment within the target region when compared to procedures which do not employ a triplex forming oligonucleotide.

The triplex-forming oligonucleotides will be further understood in view of the following non-limiting examples.

EXAMPLE 1

Targeted mutagenesis using non-modified oligonucleotides

PCT/US/07234 by Yale University, describes the use of mutagen linked, triplex forming oligonucleotides (TFOs) in site-directed mutagenesis methods (herein incorporated by reference). It has now been observed that TFOs can target mutations in vivo in the absence of a linked mutagen. Experiments were conducted that demonstrate that treatment of mammalian cells with high affinity TFOs ($K_d$ less than or equal to $2 \times 10^{-8}$) which bind to duplex DNA, can generate mutations in a target gene within a cell. Triplex-induced mutagenesis was also tested in repair-deficient human cells derived from patients with xeroderma pigmentosum, both group A (XPA) and XP variant (XPV), in order to elucidate the role of repair pathways in the observed mutagenesis. In complementary experiments, the ability of intermolecular triple helices to stimulate repair synthesis in human cell extracts was investigated.

Materials and Methods

Cells

Monkey COS cells were obtained from the American Type Culture Collection, Bethesda, Md., ATCC accession number 1651°CRL, and were maintained in Dulbecco's modified Eagle medium (DMEM) supplemented with 10% fetal calf serum (Gibco/BRL, Bethesda, Md.). Other cells were obtained from the NIGMS Human Genetic Mutant Cell Repository (Camden, N.J.). XPA cells (repository no. GM04429E) are SV40-transformed fibroblasts derived from a patient with xeroderma pigmentosum, complementation group A (XP12BE). XPV cells (GM02359) are primary fibroblasts derived from a patient with the variant form of xeroderma pigmentosum (XP115LO). Normal fibroblasts (GM00637F) are SV40-transformed cells derived from an apparently normal donor. The cells were grown in MEM supplemented with 10% fetal calf serum (Gibco/BRL, Bethesda, Md.).

Oligonucleotides and vectors

Oligonucleotides were obtained from Oligos Etc. (Wilsonville, Oreg.) or were synthesized by J. Flory of the W. M. Keck Biotechnology Resource Center at Yale using materials from Glen Research (Sterling, Va.). The sequences of oligonucleotides used in this experiment include:

| | |
|---|---|
| AG10 5' AGGAAGGGGG 3' | (Seq. ID No. 1) |
| AG20 5' AGGAAGGGGGGGGTGGTGGG 3' | (Seq. ID No. 2) |
| AG30 5' AGGAAGGGGGGGGTGGTGGG-GGAGGGGGAG 3' | (Seq. ID No. 3) |
| Mix30 5' AGTCAGTCAGTCAGTCAGTC-AGTCAGTCAG 3' | (Seq. ID No. 4) |

AG10, AG20, and AG30 were designed to bind as third strands in the anti-parallel triple helix motif to part or all of the 30 base pair polypurine/polypyrimidine site in supFG1 (P. A. Beal and P. B. Dervan, *Science* 251, 1360 (1991); A. G. Letai M. A. Palladino, E. Fromm, V. Rizzo, J. R. Fresco, *Biochemistry* 27, 9108 (1988); C. Helene, *Curr. Opinion Biotechnology* 4, 29 (1993); H. E. Moser and P. B. Dervan, *Science* 238, 645 (1987); D. Praseuth, L. Perrouault, T. Le Doan, M. Chassignol, N. Thuong, C. Helene, *Proc. Natl. Acad. Sci. USA* 85, 1349 (1988); M. Cooney, G. Czernuszewicz, E. H. Postel, S. J. Flint, M. E. Hogan, *Science* 241, 456 (1988).

Vectors

SV40 shuttle vectors, pSupFG1a and pSupFG2 were derivatives of pSP189 and carried new triplex-binding sites which were engineered into the supF gene (pSP189 was obtained from Otsuka Pharmaceutical, Bethesda, Md.). The modified supF genes were constructed by inserting synthetic oligonucleotides into the XhoI to EagI sites in the original supF gene using standard techniques as described by Sambrook et al., MOLECULAR CLONING: A LABORATORY MANUAL, second edition, Cold Spring Harbor Laboratory Press, New York (1990) (which is incorporated by reference herein).

Gel Shift Mobility Analysis

Third strand binding was measured using a gel mobility shift assay in which two complementary 57-mers containing the sequence corresponding to bp 157 to 213 of supFG1 were annealed to make a duplex target. The purine-rich oligonucleotide was end-labeled with $\alpha$-[$P^{32}$]-ATP and T4 polynucleotide kinase, mixed with the unlabeled complementary pyrimidine-rich 57-mer at a 1:1 ratio in TE buffer, incubated at 65° C. for 15 minutes and cooled to room temperature. A fixed concentration of duplex DNA ($5\times10^{-9}$ M) was incubated with increasing concentrations of oligonucleotides in 10 $\mu$l of 10 mM Tris (pH 7.4), 1 mM spermidine, and 20 mM $MgCl_2$ at 37° C. for 2 hours. The samples were analyzed by electrophoresis in an 8% polyacrylamide gel containing 89 mM Tris HCl, 89 mM boric acid, and 20 mM $MgCl_2$ at 5 V/cm for 15 hours, followed by autoradiography. A Phosphor-Imager™ (Molecular Dynamics, Sunnyvale, Calif.) was used for quantitation. The oligonucleotide concentration at which the triplex formation was half-maximal was taken as the equilibrium dissociation constant (Kd).

Mutagenesis protocol

The cells were first transfected with the SV40 vector DNA pre-mixed with cationic liposomes. Approximately $2\times10^6$ cells per dish (at a density of $5\times10^4$ per $cm^2$) were transfected by the addition to the culture medium (15 ml volume) of 5 $\mu$g of pSupFG1 DNA pre-mixed with 50 $\mu$g of cationic liposomes (DOTAP, Boehringer Mannheim, Indianapolis, Ind.). After 12 hours, the cell monolayers were washed 3 times, and fresh medium containing the selected oligonucleotide at 2 $\mu$M was added.

After 12 hours, the cells were extensively washed, and the oligonucleotides were added to the growth medium at a concentration of 2 $\mu$M. The oligonucleotides were not conjugated to any mutagen but were modified to resist nuclease-mediated degradation via incorporation of either a 3' propylamine group (Glen Research, Sterling, Va.) or phosphorothioate internucleoside linkages. Similar results were obtained with either modification.

Two days later, the vector DNA was harvested from the cells for analysis of supFG1 gene mutations. Rescue of the SV40 vector DNA and transformation of bacteria for genetic analysis of the supFG1 gene were performed as previously described (P. A. Havre and P. M. Glazer, *J. Virology* 67, 7324 (1993), C. N. Parris, D. D. Levy, J. Jessee, M. M. Seidman, *J. Mol. Biol.* 236, 491 (1994)). After isolation from the mammalian cells, the vector DNA was subjected to digestion with Dpn I to restrict any vector molecules that had not been replicated in the cells, taking advantage of the differences in mammalian and bacterial methylation patterns.

Triple-helix formation

The supercoiled pSupFG1 vector DNA was incubated with the indicated oligonucleotides in extracts that were supplemented with $\alpha$-$P^{32}$-dCTP to detect induced DNA synthesis. HeLa cell-free extracts were prepared essentially as described in P. M Glazer, S. N. Sarkar, G. E. Chisholm, and W. C. Summers, *Mol. Cell. Biol.* 7, 218 (1987). Repair synthesis assays were carried out as follows. Supercoiled pSupFG1 plasmid DNA at $2\times10^{-9}$ M plus pUC19 DNA at $5\times10^{-8}$ M (as an internal control) were pre-incubated with the oligonucleotides at $1\times10^{-6}$ M for 2 hours at 37° C. in 10 mM Tris (pH 7.4) and 10 mM $MgCl_2$. The DNA samples were added to HeLa cell extracts containing 10–15 $\mu$g/$\mu$l protein and $\alpha$-[$P^{32}$]-dCTP, additionally supplemented as described above, and incubated for 3 hours at 30° C. The DNA was extracted with phenol/chloroform, concentrated by filtration using a Centricon 100™ filter (Amicon, Beverly, Mass.), and linearized with EcoR I. The samples were analyzed by 0.7% agarose gel electrophoresis, ethidium bromide staining, and autoradiography.

DNA sequencing

The single colonies of purified mutants were picked into 5 ml of L broth containing ampicillin (50 µg/ml) and were incubated at 37° C. for 16–20 hours by shaking at 250 rpm. Cells from 3 milliliters of culture were collected by centrifugation. Isolation of plasmid DNA was accomplished using the Wizard™ plasmid miniprep DNA purification system (Promega, Madison, Wis.). 1.5 µg of plasmid DNA was used for DNA sequencing using an ABI™ cycle-sequencing kit in accordance with the manufacturer's instructions (Applied Biosystems Inc., Foster City, Calif.) using standard methods. The sequencing primer was chosen to bind to the β-lactamase gene just upstream of the supF gene in the vector.

Results

The sequence of the selected triple helix target site in the supFG1 reporter gene within the SV40 vector is presented in FIG. 1 (Seq. ID No. 5), G. Wang, D. D. Levy, M. M. Seidman, P. M. Glazer, Mol. Cell. Biol. 15, 1759 (1995)), along with the sequences of the oligonucleotides studied in these experiments (Seq. ID Nos. 1–4).

The binding of these oligonucleotides to the triplex site in supFG1 was examined using a gel mobility shift assay (R. H. Durland et al., Biochemistry 30, 9246 (1991)), in which triplex formation is detected by the reduced mobility of a radioactively-labeled, synthetic 57 bp fragment matching base pairs 157–213 in the gene.

Based on the concentration-dependence of the triplex formation, the equilibrium dissociation constants (Kd) for AG10, AG20, and AG30 were determined to be approximately $3\times10^{-5}$ M, $3\times10^{-7}$ M, and $2\times10^{-8}$ M, respectively.

These oligonucleotides were tested for their ability to induce mutations in the pSupFG1 SV40 vector within monkey COS cells (FIG. 1, Table 1).

Oligonucleotide AG30 generated mutations in the target gene at a frequency of 0.27%, 13-fold over the spontaneous background in the assay. In contrast, AG10 and AG20, which show inferior third strand binding to supFG1, were much less effective in producing mutations. As an additional control, an oligonucleotide of 30 nucleotides in length, consisting of a mixture of all 4 bases (Mix30, FIG. 1), was also tested. It does not form a detectable triple helix with supFG1, and it did not generate any mutagenesis above the background.

TABLE 1

Mutagenesis induced by triple helix formation within monkey COS cells.

| Oligonucleotide | Kd for third strand binding* | Mutants/ Total- | Mutation Frequency (%)- |
|---|---|---|---|
| None | — | 9/44,850 | 0.02 |
| Mix30 | No detectable binding | 5/16,590 | 0.03 |
| AG10 | $3 \times 10^{-5}$M | 10/14,475 | 0.07 |
| AG20 | $3 \times 10^{-7}$M | 11/10,399 | 0.11 |

TABLE 1-continued

Mutagenesis induced by triple helix formation within monkey COS cells.

| Oligonucleotide | Kd for third strand binding* | Mutants/ Total- | Mutation Frequency (%)- |
|---|---|---|---|
| AG30 | $2 \times 10^{-8}$M | 148/54,899 | 0.27 |

*Kd, equilibrium dissociation constant for triple helix formation.
-The values represent the frequency of mutations detected in the pSuPFG1 SV40-based shuttle vector following electroporation of the vector DNA into COS cells, subsequent treatment of the cells with the indicated oligonucleotides at a concentration of 2 µM, and rescue of the vectors for genetic analysis in bacteria 48 hours later.

The supFG1 mutations generated by AG30 in COS cells were examined by DNA sequence analysis (FIG. 2). Sequencing of the supFG1 gene mutations was performed directly from the plasmid vector DNA using a primer complementary to a region in the b-lactamase gene adjacent to the supFG1 gene.

Mostly point mutations, along with some deletions, were seen (FIG. 2). Notable among the point mutations were several occurrences of multiple base substitutions. Three classes of mutations were observed, including single point mutations, deletions, and multiple, simultaneous point mutations, as indicated. The base substitutions listed above the corresponding supFG1 gene sequence represent changes with respect to the upper strand. The multiple point mutations are indicated by the underlining, with each set of simultaneous changes presented on a separate line. Point mutations occurring outside of the listed sequence are indicated by position numbers, with the involved base changes given. The deletions are presented below the gene sequence, with the deletion endpoints indicated.

To investigate a possible role for DNA repair in the triplex-induced mutagenesis, the ability of these TFOs to cause mutations within both repair-deficient (XPA and XPV) and repair-proficient (normal fibroblasts) human cells was examined (Table 2).

In the XPA cells, which have a defect in the DNA damage recognition protein that is a component of a ternary repair endonuclease complex, no triple helix-targeted mutagenesis was seen (C. H. Park and A. Sancar, Proc. Natl. Acad. Sci. USA 91, 5017 (1994); C. J. Jones and R. D. Wood, Biochemistry 32, 12096 (1993)).

TABLE 2

Mutagenesis induced by triple helix formation in human repair-deficient and repair-proficient cell lines.

| Cell line* | Oligonucleotide- | Mutants/ Total- | Mutation Frequency (%)- |
|---|---|---|---|
| Normal fibroblasts | None | 5/12,250 | 0.04 |
|  | Mix30 | n.d. | n.d. |
|  | AG30 | 50/21,575 | 0.23 |
| XPA | None | 13/48,329 | 0.03 |
|  | Mix30 | 14/42,500 | 0.03 |
|  | AG30 | 9/32,750 | 0.03 |
| XPV | None | 0/8,350 | <0.01 |
|  | Mix30 | 4/6,895 | 0.06 |

TABLE 2-continued

Mutagenesis induced by triple helix formation in human repair-deficient and repair-proficient cell lines.

| Cell line* | Oligonucleotide- | Mutants/ Total- | Mutation Frequency (%)- |
|---|---|---|---|
| | AG30 | 71/8,704 | 0.82 |

*XPA, fibroblasts derived from a patient with xeroderma pigmentosum, complementation group A; XPV, fibroblasts derived from a patient with xeroderma pigmentosum variant.
-AG30 binds strongly as a third strand to the target supFG1 gene (Kd = 2 × $10^{-8}$M), whereas Mix30 shows no detectable binding.
-The values represent the frequency of mutations detected in the pSupFG1 SV40-based shuttle vector following electroporation of the vector DNA into the indicated cells, subsequent treatment of the cells with the indicated oligonucleotides at a concentration of 2 μM, and rescue of the vectors for genetic analysis in bacteria 48 hours later.
n.d., not determined.

The mechanism by which the triple helix formation induces mutations was further investigated by testing the ability of triple helices to stimulate repair synthesis on the vector template in HeLa cell-free extracts (R. D. Wood, P. Robins, T. Lindahl, *Cell* 53, 97 (1988), Sibghat-Ullah, I. Husain, W. Carlton, A. Sancar, *Nucleic Acids Res.* 17, 447 (1989); M. K. K. Shivji, M. K. Kenny, R. D. Wood, *Cell* 69, 367 (1992); J. T. Reardon, P. Speilmann, J. Huang, S. Sastry, A. Sancar, J. E. Hearst, *Nucleic Acids Res.* 19, 4623 (1991)).

This type of protocol has been used to study repair synthesis associated with UV and chemical damage and to isolate factors involved in nucleotide excision repair. As an internal control, pUC19 plasmid DNA (which lacks the triplex target site) was included along with pSupFG1 DNA in all samples. Following incubation in the extracts, the plasmids were linearized by digestion with EcoR I and analyzed by agarose gel electrophoresis. The DNA in each sample was visualized by ethidium bromide-staining to show that the quantities of the pSupFG1 and pUC19 DNAs were essentially constant in all the samples.

Incorporation of the labeled nucleotide into the plasmid DNA was determined by autoradiography. AG30 and, to a lesser extent, AG20, stimulated labeling of pSupFG1 but not of pUC19, consistent with high affinity, sequence-specific triplex formation by these two TFOs. Neither AG10, which binds poorly to pSupFG1 (at the 0.25 μM concentration in the extract reactions), nor Mix30, which does not bind at all, induced any repair synthesis above background. Hence, there appears to be a repair activity in the HeLa extracts that recognizes a tightly bound third stand as a lesion, leading to repair synthesis and label incorporation. Stimulation of label incorporation occurs with oligonucleotides that are substituted at the 3' end with a propylamine group, and so the argument that the oligonucleotides simply serve as primers can be ruled out.

The data presented here demonstrate that high affinity, oligonucleotide-mediated triple helix formation is mutagenic in mammalian cells, via a pathway that may involve specific repair activities.

Although significantly above background, the frequency of triplex-induced mutations reported here (in the range of 0.2 to 0.8%) is still somewhat lower than the targeted mutation frequency observed when TFOs are used to deliver a tethered psoralen molecule to a target site within cells (2.1%, See PCT/US94/07234). Since psoralen is a highly reactive mutagen upon photoactivation, it is not surprising that a triplex-targeted psoralen adduct is more effective in inducing mutations than is triple helix formation alone. However, genetic manipulation using such mutagen-conjugated TFOs requires either control over the reactivity of the mutagen (as with photoactivation) or entails the risk of non-specific reactivity of the tethered reagent. The ability of oligonucleotides without any tethered reactive group to generate mutations in a target gene overcomes these potential drawbacks. It offers the possibility of highly specific genetic manipulation using appropriately designed oligonucleotides that bind with high affinity to their target sites.

Modifications and variations of the present invention, mutagenic triplex-forming oligonucleotides, as well as methods of use thereof, will be obvious to those skilled in the art from the foregoing detailed description. Such modifications and variations are intended to come within the scope of the appended claims.

We claim:

1. A mutagenic composition comprising a carrier suitable for administration to cells and an effective amount of a high affinity oligonucleotide for targeted mutagenesis of a double-stranded nucleic acid molecule, the single-stranded oligonucleotide having a sequence that forms a triple-stranded nucleic acid molecule with a target region of the double-stranded nucleic acid molecule adjacent to a site where a mutation in the target region induced by triple helix formation will activate, inactivate or alter the activity or function of the double-stranded nucleic acid molecule or the protein it encodes, wherein the oligonucleotide has a $K_d$ of $2\times10^{-8}$ or less for the target region, in combination with a recombination fragment.

2. The mutagenic composition of claim 1 wherein the oligonucleotide is made synthetically.

3. The composition of claim 1 wherein the oligonucleotide is at least 20 nucleotide residues in length.

4. The composition of claim 1 wherein the triple-helix forming oligonucleotide is linked to a mutagenic compound.

5. The composition of claim 1 wherein the double-stranded nucleic acid molecule encodes a biologically active protein and the targeted mutagenesis alters the activity of the protein.

6. The composition of claim 5 wherein the double-stranded nucleic acid molecule is a gene.

7. The composition of claim 6 wherein the gene is an oncogene.

8. The composition of claim 6 wherein the gene is a defective gene.

9. The composition of claim 5 wherein the double-stranded nucleic acid molecule is all or a portion of a viral genome.

10. A method of producing a high affinity, triple-helix forming oligonucleotide composition comprising the step of synthesizing an oligonucleotide substantially complementary, based on the third strand binding code, to a target region of a double-stranded nucleic acid molecule adjacent to a site where a mutation in the target region will activate, inactivate or alter the activity or function of the double-stranded nucleic acid molecule or the protein it encodes, wherein the disassociation constant for the oligonucleotide and the target region is less than or equal to $2\times10^{-8}$, and adding to the triple-helix forming oligonucleotide a recombination fragment.

11. The method of claim 10, wherein the oligonucleotide is at least 20 nucleotide residues in length.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 10 bases
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

AGGAAGGGGG                                                         10

(2) INFORMATION FOR SEQ ID NO:2:

(i) SEQUENCE CHARACTERISTICS:
      (A) LENGTH: 20 bases
      (B) TYPE: nucleic acid
      (C) STRANDEDNESS: single -continued (D) TOPOLOGY: linear (ii) MOLECULE TYPE: DNA (xi) SEQUENCE DESCRIPTION: SEQ ID NO:2:

AGGAAGGGGG GGGTGGTGGG                                                  20

(2) INFORMATION FOR SEQ ID NO:3:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

AGGAAGGGGG GGGTGGTGGG GGAGGGGGAT                                       30

(2) INFORMATION FOR SEQ ID NO:4:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

AGTCAGTCAG TCAGTCAGTC AGTCAGTCAG                                       30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:5:

TCCTTCCCCC CCCACCACCC CCTCCCCCTC                                       30

(2) INFORMATION FOR SEQ ID NO:6:

(i) SEQUENCE CHARACTERISTICS:
        (A) LENGTH: 124 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:6:

GAATTCGAGA GCCCTGCTCG AGCTGTGGTG GGGTTCCCGA GCGGCCAAAG GGAGCAGACT      60

CTAAATCTGC CGTCATCGAC TTCGAAGGTT CGAATCCTTC CCCCCCCACC ACCCCCTCCC    120

CCTC                                                                 124